(12) United States Patent
Hoang et al.

(10) Patent No.: US 8,425,628 B2
(45) Date of Patent: Apr. 23, 2013

(54) NO-SULFUR FUEL LUBRICITY ADDITIVE

(75) Inventors: Viet Q. Hoang, Houston, TX (US);
Philip L. Leung, Houston, TX (US);
Gordon T. Rivers, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 0 days.

(21) Appl. No.: 13/597,367

(22) Filed: Aug. 29, 2012

(65) Prior Publication Data

US 2012/0317876 A1 Dec. 20, 2012

Related U.S. Application Data

(62) Division of application No. 12/875,352, filed on Sep. 3, 2010, now Pat. No. 8,262, 749.

(60) Provisional application No. 61/242,161, filed on Sep. 14, 2009.

(51) Int. Cl.
*C10L 1/19* (2006.01)
*C07C 67/00* (2006.01)

(52) U.S. Cl.
USPC .............................. 44/389; 560/204; 44/385

(58) Field of Classification Search ............... 44/389, 44/385; 560/204
See application file for complete search history.

(56) References Cited

U.S. PATENT DOCUMENTS

| | | | |
|---|---|---|---|
| 2,985,522 A | 5/1961 | Binning et al. | |
| 3,287,273 A | 11/1966 | Furey et al. | |
| 3,522,022 A | 7/1970 | May et al. | |
| 4,474,579 A | 10/1984 | Wilderson et al. | |
| 4,857,073 A | 8/1989 | Vataru et al. | |
| 6,129,772 A | 10/2000 | Weers et al. | |
| 6,482,977 B1 * | 11/2002 | Whitney et al. | 560/221 |
| 6,793,695 B2 | 9/2004 | Wilkes et al. | |
| 7,402,185 B2 | 7/2008 | Aradi et al. | |
| 8,262,749 B2 | 9/2012 | Hoang et al. | |
| 2004/0010967 A1 | 1/2004 | Aradi et al. | |
| 2004/0154218 A1 | 8/2004 | Watanabe et al. | |
| 2004/0255511 A1 | 12/2004 | Krull et al. | |
| 2005/0000152 A1 | 1/2005 | Krull et al. | |
| 2005/0197255 A1 | 9/2005 | Otto et al. | |
| 2006/0288638 A1 | 12/2006 | Schwab | |
| 2007/0094920 A1 | 5/2007 | Ahlers et al. | |
| 2009/0056203 A1 | 3/2009 | Schield et al. | |

FOREIGN PATENT DOCUMENTS

| | | |
|---|---|---|
| EP | 0798365 A1 | 10/1997 |
| EP | 1591466 A1 | 11/2005 |

* cited by examiner

*Primary Examiner* — Cephia D Toomer

(74) *Attorney, Agent, or Firm* — Mossman Kumar & Tyler PC

(57) ABSTRACT

Reacting an alkylene carbonate, such as ethylene carbonate, with dimer acid in the presence of a catalyst, such as a tertiary amine catalyst, gives a dimer acid diester having essentially no sulfur, and thus may be added to ultra-low sulfur diesel fuel downstream of a refinery. The diester enhances the lubricity properties of hydrocarbon fuels, increases their service life and fuel efficiency. The manufacturing process time may be decreased significantly compared with a process using ethylene glycol instead of ethylene carbonate, and much less ethylene glycol by-product results.

11 Claims, No Drawings

NO-SULFUR FUEL LUBRICITY ADDITIVE

CROSS-REFERENCE TO RELATED APPLICATION

This application is a divisional application from U.S. patent application Ser. No. 12/875,352 filed Sep. 3, 2010, issued Sep. 11, 2012 as U.S. Pat. No. 8,262,749, which in turn claims the benefit of U.S. Provisional Application No. 61/242,161 filed Sep. 14, 2009, all of which are incorporated herein by reference.

TECHNICAL FIELD

The present invention relates to methods and compositions for improving lubricity in hydrocarbon fuels, and more particularly relates, in one non-limiting embodiment, to methods and compositions for hydrocarbon fuel lubricity additives having essentially no sulfur.

BACKGROUND

It is well known that in many engines the fuel is also the lubricant for the fuel system components, such as fuel pumps and injectors. Many studies of fuels with poor lubricity have been conducted in an effort to understand fuel compositions that have poor lubricity and to correlate lab test methods with actual field use. The problem is general to diesel fuels, kerosene and gasolines, however, most of the studies have concentrated on the first two hydrocarbons.

Previous work has shown that saturated, monomeric and dimeric, fatty acids of from 12 to 54 carbon atoms used individually give excellent performance as fuel lubricity aids in diesel fuels. Fatty acids are for the most part unbranched. A number of other kinds of lubricity additives are also known. Since the advent of low sulfur diesel fuels in the early 1990s, relatively large amounts of these lubricity additives have been used to provide a fuel that does not cause excessive wear of engine parts.

Unfortunately, many commercially available fatty acids and fatty acid blends tend to freeze or form crystals at temperatures common during winter weather. The freezing or formation of crystals makes handling of the additives, and particularly injection into fuel, difficult. Blending the fatty acid with a solvent can lower the freezing point and reduce the crystal formation temperature, or cloud point. However, addition of a solvent may increase cost and preparation complexity.

Some of the fatty acids, fatty acid ammonium salts and fatty acid amides presently used may have the disadvantage of solidifying on storage at low temperatures. Often even at room temperature, crystalline fractions may separate and cause handling problems. Diluting the additives with organic solvents only partly solves the problem, since fractions may still crystallize out from solutions or the solution may gel and solidify. Thus, for use as lubricity additives, the fatty acids, fatty acid ammonium salts and fatty acid amides either have to be greatly diluted or kept in heated storage vessels and added via heated pipework.

It is also known to make fuel lubricity additives by reacting alkylene glycols with monomeric and dimeric carboxylic acids using sulfur-containing catalysts such as toluene sulfonic acid. However, this method takes considerable time, on the order of 40 to 60 hours, produces significant amounts of alkylene glycol and water as by-products and leaves certain amounts of sulfur in the additive which undesirably wind up in the hydrocarbon fuel. Further, as environmental regulations have become more stringent, low sulfur fuels are mandated to have increasingly lower amounts of sulfur present and even the small amounts present in these additives become problematic.

Thus, it would be desirable if a way could be discovered to enhance the lubricity of distillate fuels, but that involved essentially no sulfur. Further, it would be helpful if a no-sulfur fuel additive could be made by a process relatively quickly without large amounts of by-products.

SUMMARY

There is provided, in one non-limiting form, a dimer acid diester fuel lubricity additive having the formula (I):

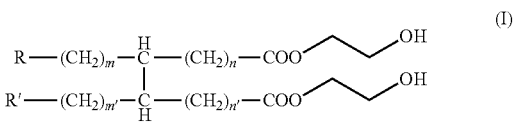

where: R and R' are the same or different, saturated, unsaturated or polyunsaturated, straight or branched alkyl groups having from 1 to 30 carbon atoms;
n, m, n' and m' are the same or different, ranging from 0 to 20; and
there may be more than one C—C crosslink between the monofunctional carboxylic acid moieties.

Alternatively there is provided in one non-restrictive embodiment a fuel lubricity additive produced by reacting a first reactant, such as an alkylene carbonate, an alkylene sulfite, an alkylene thionocarbonate and mixtures thereof, with dimer acid in the presence of a catalyst. The catalyst may be a tertiary amine or a weakly basic metal oxide or metal hydroxide, where the metal is chosen from the alkaline earth metals, the transition metals and/or the lanthanide metals. "Weakly basic" is defined as having a pK-b greater than 1. Strongly basic alkali metal hydroxides have also been tried with some success, where a strongly basic catalyst is defined herein as having a pK-b less than 1, such as NaOH.

In another non-limiting version there is provided a method for producing a fuel lubricity additive comprising reacting ethylene carbonate with dimer acid in the presence of a catalyst as described above.

Further there is provided in one non-restrictive embodiment a hydrocarbon fuel containing a fuel lubricity additive, where the fuel lubricity additive in turn is a dimer acid diester having the formula (I):

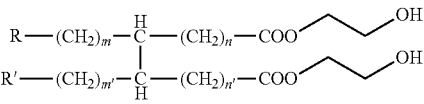

where R and R' are the same or different, saturated, unsaturated or polyunsaturated, straight or branched alkyl groups having from 1 to 30 carbon atoms, and n, m, n' and m' are the same or different, ranging from 0 to 20, and there may be more than one C—C crosslink between the monofunctional carboxylic acid moieties. The amount of the fuel lubricity additive is effective to improve the lubricity of the hydrocarbon fuel as compared to an otherwise identical fuel absent the fuel lubricity additive.

DETAILED DESCRIPTION

A hydrocarbon fuel lubricity additive has been discovered that has essentially no sulfur and which may be made by a process that is relatively fast and which produces relatively small amounts of by-products that require significant expenditure of time, energy, and other resources for their removal compared to previously known methods. Previously, dimers of carboxylic acids were reacted with alkylene glycols (e.g. ethylene glycol) in the presence of a sulfur-containing catalyst (e.g. toluene sulfonic acid). It has been discovered that the reaction of an alkylene carbonate (e.g. ethylene carbonate) with the same kind of dimers of carboxylic acids in the presence of a catalyst gives significant advantages. Table I compares the old and new processes.

TABLE I

Comparison of Hydrocarbon Fuel Lubricity Additive Production Processes

|  | Old Formula and Process | New Formula and Process |
| --- | --- | --- |
| Reactants: | Dimer acid + ethylene glycol (EG) | Dimer acid + ethylene carbonate |
| Catalyst: | Sulfonic acid | Tertiary amine |
| Main by-products: | Water | $CO_2$ |
| Other by-products: | Significant amounts of EG and water | Minor or small amounts of EG and water |
| Excess reactant needed | As much as 20%+ excess equivalence (1.2+ to 1) of EG to dimer acid is needed to control the amount of undesirable polymer or polyester formed | Equal equivalent amounts of both reactants used. No waste of reactant. |
| Undesirable "higher" esters | A certain amount of higher esters is formed | Less higher esters formed |
| Removal of excess raw material | Much EG needs to be removed as waste | Minimal amounts of water and EG formed as minor amounts of by-products |
| Process time | About 50-60 hours | About 6-8 hours |
| Sulfur content | Since sulfonic acid is needed for catalysis, the sulfur content is increased and may cause the product to be out of specification. | Since an environmentally friendly and safe tertiary amine catalyst is used, there is no increase in sulfur content |
| Solvent requirement | 15-20% solvent needed for condensate removal | No solvent needed |
| "QC" tests needed to ensure product quality | Acid Number Test Hydroxyl Number Test IPA Test Solvent Test | Acid Number Test |
| Careful pre-weighing of catalyst | Due to the need to carefully control the amount of sulfur introduced with the catalyst, time-consuming careful pre-weighing of catalyst is required | Not required (no sulfur introduced) |
| By-product disposal of the distillate per federal, state and local regulations | Required (a mixture of water, glycol and solvent) | Not required (other than $CO_2$) |
| Ester formation Time | 15 to 20 hours | 3 hours |
| Distillation time | 25 hours | 1 hour |
| Addition of too much catalyst | Product becomes useless with the low sulfur fuel regulation set by the US government | No problem |
| Average sulfur ppm in final product | 11.6 | 0-2.5 |
| Average acid number | 3.3 | <2 |
| Number of tests required from QC | 10 | 3 |
| Number of raw materials required for processing | 4 | 3 |
| Batch yield | 92% | 94% |
| Final product color | Clear amber | Clear amber |
| Energy usage | Much more needed for long process and distillation to remove excess raw material | Much less energy needed for the much shorter process time |
| Raw material wastage | Excess raw material wasted | No excess, no waste |

TABLE I-continued

Comparison of Hydrocarbon Fuel Lubricity Additive Production Processes

|  | Old Formula and Process | New Formula and Process |
| --- | --- | --- |
| Process sensitivity | Sensitive to small upsets in material balance and process deviation | Much less sensitive |

In one non-limiting embodiment the fuel lubricity additives described herein are approximately 75% active esters, or even up to 100% active esters, made by reacting dimer acid and ethylene carbonate using dimethylcocoamine as a catalyst. The diester product is useful as a lubricity additive in hydrocarbon fuels, particularly low sulfur diesel fuels. This low sulfur, low acid number lubricity additive is an effective fuel lubricity improver which enhances performance of the fuel's lubricity qualities, increases service life and efficiency of fuel, and can be added to ultra-low or no sulfur diesel fuel downstream of the refinery. This product also meets the new low sulfur fuel regulation set by the U.S. government.

In one non-limiting embodiment the fuel lubricity additive has less than 10 ppm sulfur, alternatively less than 5 ppm sulfur, further 3 ppm sulfur or less. Of course, if the fuel lubricity additive contained no sulfur (0 ppm), this would be particularly suitable. In another non-restrictive version, the acid number of the fuel lubricity additive is less than 5, alternatively less than 2. Acid number (or "neutralization number" or "acid value" or "acidity") is the mass of potassium (KOH) in milligrams that is required to neutralize one gram of a chemical. The acid number is a measure of the amount of carboxylic acid groups in a chemical compound, such as a fatty acid or in a mixture of compounds.

One non-restrictive embodiment of the reaction herein may be schematically illustrated as shown:

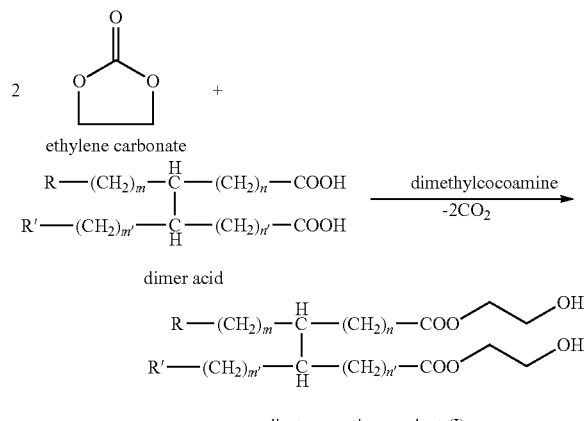

Other alkylene carbonate reactants besides ethylene carbonate would be expected to be useful, for instance propylene carbonate, butylene carbonate, and the like. These carbonates, particularly ethylene carbonate, are widely available commercially. Alternative or additional reactants to be used in place of or together with alkylene carbonate, respectively, include, but are not necessarily limited to alkylene sulfites, alkylene thionocarbonates and combinations thereof, where the alkylene groups are the same as those noted below. However, it may be that if alkylene sulfites or alkylene thionocarbonates are used, the amount of sulfur in the fuel lubricity additive may increase. In some embodiments, alkylene glycols, including, but not necessarily limited to ethylene glycol and/or propylene glycol, may be used in addition to or in place of ethylene carbonate and the other first reactants.

The dimer acid reactant is commonly known and has the formula:

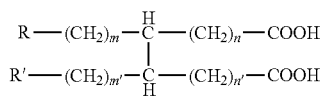

where R and R' are the same or different, saturated, unsaturated or polyunsaturated, straight or branched alkyl groups having from 1 independently to 30 carbon atoms, and n, m, n' and m' are the same or different, ranging from 0 to 20. There may be more than one C—C crosslink between the monofunctional carboxylic acid moieties. Alternatively, R and R' are the same or different, saturated, unsaturated or polyunsaturated, straight alkyl groups having from 1 independently to 20 carbon atoms, or having from 1 independently to 8 carbon atoms; n and m are the same or different, ranging from 1 independently to 10, or ranging from 4 independently to 16. In other non-limiting embodiments R may be butyl and R' may be octyl; n may be 8 and m may be 14.

In another non-limiting embodiment, the dimer acid may have the definition found in U.S. Pat. No. 3,287,273, incorporated herein in its entirety by reference. Such commercial dimer acids are generally produced by the polymerization of unsaturated $C_{18}$ fatty acids to form $C_{36}$ dibasic dimer acids. Depending on the raw materials used in the process, the $C_{18}$ monomeric acid may be linoleic acid or oleic acid or mixtures thereof. The resulting dimer acids may therefore be the dimers of linoleic acid, oleic acid or a mixture thereof. In a different non-limiting embodiment, dimer acid may be available commercially as PRIPOL™ 1029 from Croda International Plc (formerly Uniquema).

Consequently, the diester fuel lubricity additive reaction product may have the following formula (I), in one non-limiting embodiment:

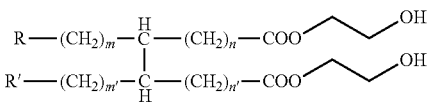

where R and R' are the same or different, saturated, unsaturated or polyunsaturated, straight or branched alkyl groups having from 1 to 30 carbon atoms and n, m, n' and m' are the same or different, ranging from 0 to 20, and there may be more than one C—C crosslink between the monofunctional carboxylic acid moieties. Alternatively, R and R' may be the same or different, saturated, unsaturated or polyunsaturated, straight alkyl groups having from 1 independently to 20 carbon atoms, or having from 1 independently to 16 carbon atoms, or from 1 to 10, where n, m, n' and m' are the same or different, ranging from 1 independently to 10, or ranging from 4 independently to 16.

The catalyst discovered to be useful for the reaction to make the fuel lubricity additives herein may be a tertiary amine catalyst and/or a weakly basic metal oxide or metal hydroxide. Dimethylcocoamine is a particularly suitable tertiary amine catalyst, although other catalysts of a similar structure may be useful, for instance a tertiary amine where one or two substituents on the nitrogen atom are relatively short alkyl groups, for instance methyl and/or ethyl, and the third substituent is a relatively long alkyl group (straight or branched), in one non-restrictive embodiment having from 4 to 30 carbon atoms. Dialkylcocoamines may be useful alternative tertiary amine catalysts where the alkyl group is straight or branched and has from 1 to 4 carbon atoms (lower alkyl). The amount of catalyst used may range from about 0.01 to about 0.1 mole of amine per mole of dimer acid. Other potential catalysts which were tried for this reaction and which did not give acceptable results include HCl, NaOH, KOH, $H_3PO_3$, $NH_4OH$, dodecyl benzene sulfonic acid (DDBSA), and para-toluene sulfonic acid (PTSA). Of course, as previously noted, PTSA is not preferred as a catalyst because it leaves residual sulfur in the product, which is undesirable in the ultimate end-use hydrocarbon fuel.

In the case of weakly basic metal oxide or metal hydroxides, the metal in these catalysts may be an alkaline earth metal, a transition metal and/or a lanthanide metal. Suitable alkaline earth metals include, but are not necessarily limited to, magnesium, calcium, barium and the like. Suitable transition metals include, but are not necessarily limited to, scandium and the like. Suitable lanthanide metals include, but are not necessarily limited to, lanthanum, cerium and the like.

In one non-limiting embodiment, the molar ratio of alkylene carbonate to dicarboxylic acid (e.g. dimer acid to ethylene carbonate) ranges from about 1.0:1 independently to about 2.2:1. Alternatively, this molar ratio is about 1:1.

The reaction may be conducted at a temperature in the range from about 100 to about 170° C., in one non-restrictive version. Alternatively, the temperature may range from about 160 independently to about 165° C. (By "independently" it is meant herein that any lower threshold to the range may be paired with any upper threshold noted and vice versa.) In one non-limiting embodiment the reaction may be conducted at vacuum (reduced pressure) or ambient pressure, or a pressure above ambient, but a nitrogen sparge is used to remove the by products. Alternatively, the reaction may be conducted from 15 to 30 inches of Hg absolute.

Suitable solvents to be used in conjunction with the fuel lubricity additives prepared herein may include, but not necessarily be limited to, aromatic solvents and/or pure paraffinic solvents and/or, high boiling ketone-type or ether-type solvents and mixtures thereof. Aromatic solvents are particularly suitable in one non-limiting embodiment. The proportion of solvent in the total fuel lubricity aid composition may range from about 0 to 90 weight %. The use of an inert or non-reactive solvent is optional. Specific examples of suitable paraffinic or non-aromatic solvents include, but are not limited to paraffins and cycloparaffins, kerosene, diesel, gasoline, and the like and blends thereof. Suitable examples of aromatic solvents may include, but are not necessarily limited to, aromatic naphtha, xylene, toluene, isopropyl benzene, mesitylene, ethylbenzene, and the like and blends thereof. Blends of non-aromatic and aromatic solvents may be suitably used.

In another non-limiting embodiment the fuel lubricity additive may be prepared using the following procedure of Table II, which is not intended to limit the invention in any way, but rather to more completely illustrate it. In this non-restrictive version, the reactants are dimer acid and ethylene carbonate, being reacted together in the presence of dimethylcocoamine catalyst.

TABLE II

A. GENERAL INSTRUCTIONS -- Be sure that the reaction vessel is clean, dry, and free of sulfur-containing residue.
B. ADDITION OF DIMER ACID (PRIPOL 1029), and DIMETHYL COCOAMINE
   NOTE: PRIPOL 1029 needs to be hot boxed in order to lower its viscosity
   for easy charging to the reactor.
   1. Turn on vacuum and pull 15-20 inches vacuum (about 51 to about 68 kPa)
      on the reactor.
   2. Charge: 59.27 pounds (26.9 kg) PRIPOL 1029 to the vessel.
   3. Charge: 0.5 pounds (0.2 kg) dimethylcocoamine catalyst to the
      vessel.
   4. Turn on an agitator.
   5. Heat to 50° C.
C. ADDITION OF ETHYLENE CARBONATE
   1. At 50° C., add: 18.03 pounds (8.2 kg) of ethylene carbonate which
      has been previously "hot boxed".
   2. Break the vacuum in the reactor to 0 psig with above surface
      nitrogen.
   3. Purge low flow nitrogen above surface.
   4. Heat to 165° C.
   5. Hold at 165° C. for 3 hours.
   6. Sample after 3 hours for the acid number. The specification is <2.
      NOTE: If the acid number is >2, repeat step C-5 for 30 minutes until
      acid number <2. Then continue to Step D.
D. ADDITION OF U-14 (SOLVENT 14)
   1. Cool to 130° C.
   2. Stop flow nitrogen above surface
      Add: U-14 (Solvent 14) 22.20%
E. DEHYDRATION
   1. Drain and close the solvent return line from the decanter.
   2. Set temperature to 130° C.
   3. Pull 15"-20" vacuum on the reactor through the condenser/decanter
      system with above surface nitrogen purge.

TABLE II-continued

4. Hold at 125-130° C. at 15"-20" vacuum and nitrogen purge for 30 minutes or until no more condensate is distilled. Drain distillate as needed.
5. Cool to 45° C. and proceed to F-1

F. PRODUCT DISCHARGE
1. Turn off agitator, and discharge. The finished product is a clear, amber liquid.

It is expected that if this method is followed, the resulting fuel lubricity additive will contain essentially no sulfur, which is defined herein as less than 10 ppm sulfur, alternatively less than 5 ppm sulfur, further 3 ppm sulfur or less, even 0 ppm sulfur.

Shown in Table III are the results of lubricity testing on various additives; lower numbers are better. Colonial Pipeline ULSD refers to a known Ultra Low Sulfur Diesel (ULSD) fuel used in all of the testing for which results are reported in Table III. It may be seen that for the 100 ppm and 125 dosage levels that the Example 1 material, made according to the present process, performed the best.

Example 1 material is the monoester for ethylene glycol (dimer acid diester) made by the process described herein, that is the new process of Table I and the specific process outlined in Table II.

Example 2 material is made by a process of reacting 2,6-di-tert-butylphenol, PRIPOL 1029, ethylene glycol, DDBSA and solvent.

Example 3 material is made using RADIA 0951, solvent, ethylene glycol and sulfuric acid catalyst.

Example 4 material is made using RADIA 0951, solvent, ethylene glycol and DDBSA catalyst.

RADIA 0951 is a dimer acid available from Oleon Americas comparable to PRIPOL 1029.

TABLE III

Lubricity Performance

| Sample Fuel | Dosage, ppm | Ex. 1 | Ex. 2 | Ex. 3 | Ex. 4 |
|---|---|---|---|---|---|
| Colonial Pipeline ULSD | 0 | 597 | 597 | 597 | 597 |
| Colonial Pipeline ULSD | 75 | — | — | — | — |
| Colonial Pipeline ULSD | 100 | 471 | 573 | 554 | — |
| Colonial Pipeline ULSD | 125 | 407 | 470 | 453 | 546 |
| Colonial Pipeline ULSD | 150 | — | — | 381 | 415 |

The compositions and methods described herein relate to lubricity additive compositions for distillate fuels, as contrasted with products from resid. In the context herein, distillate fuels include, but are not necessarily limited to diesel fuel, kerosene, gasoline and the like. It will be appreciated that distillate fuels include blends of conventional hydrocarbons meant by these terms with oxygenates, e.g. alcohols, such as methanol, ethanol, and other additives or blending components presently used in these distillate fuels, or that may be used in the future. In one non-limiting particular embodiment, the methods and compositions herein relate to low sulfur fuels, which are defined as having a sulfur content of 0.2% by weight or less, and in another non-limiting embodiment as having a sulfur content of about 0.0015 wt. % or less—such as the so-called "ultra low sulfur" fuels. Particularly preferred hydrocarbon fuels herein are diesel and kerosene, and in one non-restrictive version, ultra low sulfur diesel (ULSD) fuels.

In one non-limiting embodiment of the methods and compositions, the lubricity additive in the total distillate fuel should at least be an amount to improve the lubricity of the distillate fuel as compared to an identical distillate fuel absent the additive. Alternatively, the amount of additive may range from about 1 to about 500 ppm, and in an alternate embodiment, the lower threshold may be about 75 ppm and the upper threshold may independently be about 200 ppm.

Other, optional components may be added independently to the distillate fuels. In non-limiting embodiments these may include, but are not necessarily limited to, detergents, pour point depressants, cetane improvers, dehazers, cold operability additives, conductivity additives, corrosion inhibitors, biocides, dyes, and mixtures thereof. In another non-limiting embodiment of the methods and compositions herein, water is explicitly absent from the inventive composition.

In the foregoing specification, the methods and compositions herein have been described with reference to specific embodiments thereof, and have been demonstrated as effective for improving the lubricity of fuels. However, it will be evident that various modifications and changes can be made thereto without departing from the broader spirit or scope of the invention as set forth in the appended claims. Accordingly, the specification is to be regarded in an illustrative rather than a restrictive sense. For example, specific combinations of dimerized carboxylic acids with alkylene carbonates in the presence of other catalysts, but not specifically identified or tried in a particular reaction may give products useful to improve the lubricity of fuels herein, and are anticipated to be within the scope of this invention. It is expected that the compositions of this invention may also impart to the engines in which they are used as fuel lubricity aids, greater horsepower, lower emissions and/or better fuel economy as a result of less friction, whether they are used in diesel or gasoline engines.

The words "comprising" and "comprises" as used throughout is to interpreted "including but not limited to".

The present invention may suitably comprise, consist or consist essentially of the elements disclosed and may be practiced in the absence of an element not disclosed. For example, the fuel lubricity additive may consist of or consist essentially of, reacting an alkylene carbonate with dimer acid in the presence of a tertiary amine catalyst.

What is claimed is:

1. A fuel lubricity additive produced by a process comprising reacting an alkylene carbonate with a dimer acid reactant in the presence of a catalyst selected from the group consisting of tertiary amines, metal oxides, metal hydroxides, and combinations thereof, where the metal in the metal oxides and metal hydroxides are selected from the group consisting of alkaline earth metals, transition metals, lanthanide metals and combinations thereof.

2. The fuel lubricity additive of claim 1 where the molar ratio of alkylene carbonate the reactant to the dimer acid reactant ranges from about 1.0:1 to about 2.2:1.

3. The fuel lubricity additive of claim 1 where the catalyst is a tertiary amine that is a dialkylcocoamine.

4. The fuel lubricity additive of claim 1 where the reacting is conducted at a temperature in the range from about 100 to about 170° C.

5. The fuel lubricity additive of claim 1 where the alkylene carbonate is ethylene carbonate and the fuel lubricity additive has the formula:

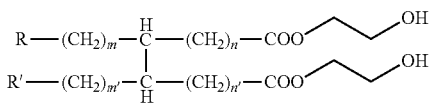

where: R and R' are the same or different, saturated, unsaturated or polyunsaturated, straight or branched alkyl groups having from 1 to 30 carbon atoms; and
n, m, n' and m' are the same or different, ranging from 0 to 20.

6. The fuel lubricity additive of claim 5 where:
R and R' are the same or different, saturated, unsaturated or polyunsaturated, straight alkyl groups having from 1 to 8 carbon atoms;
n, m, n' and m' are the same or different, ranging from 4 to 16; and
there may be more than one C—C crosslink between the monofunctional carboxylic acid moieties.

7. A hydrocarbon fuel comprising a fuel lubricity additive produced by a process comprising reacting an alkylene carbonate with a dimer acid reactant in the presence of a catalyst selected from the group consisting of tertiary amines, metal oxides, metal hydroxides, and combinations thereof, where the metal in the metal oxides and metal hydroxides are selected from the group consisting of alkaline earth metals, transition metals, lanthanide metals and combinations thereof where the amount of the fuel lubricity additive is effective to improve the lubricity of the hydrocarbon fuel as compared to an otherwise identical fuel absent the fuel lubricity additive.

8. The hydrocarbon fuel of claim 7 where the amount of the fuel lubricity additive ranges from about 1 to about 500 ppm based on the total amount of hydrocarbon fuel.

9. The hydrocarbon fuel of claim 7 where in the fuel lubricity additive the first reactant is ethylene carbonate and the fuel lubricity additive comprises a dimer acid diester having the formula:

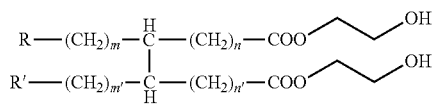

where: R and R' are the same or different, saturated, unsaturated or polyunsaturated, straight or branched alkyl groups having from 1 to 30 carbon atoms; and
n, m, n' and m' are the same or different, ranging from 0 to 20.

10. The hydrocarbon fuel of claim 9 where:
R and R' are the same or different, saturated, unsaturated or polyunsaturated, straight alkyl groups having from 1 to 8 carbon atoms;
n, m, n' and m' are the same or different, ranging from 4 to 16; and
there may be more than one C—C crosslink between the monofunctional carboxylic acid moieties.

11. The hydrocarbon fuel of claim 7 where the fuel lubricity additive has an amount of sulfur of less than 10 ppm.

* * * * *